(12) United States Patent
Reyes et al.

(10) Patent No.: US 12,685,669 B2
(45) Date of Patent: Jul. 21, 2026

(54) REDUCED VIBRATION VITRECTOMY PROBE

(71) Applicant: Alcon Inc., Fribourg (CH)

(72) Inventors: Nathaniel Reyes, Santa Ana, CA (US); John R. Underwood, Laguna Nigel, CA (US)

(73) Assignee: Alcon Inc., Fribourg (CH)

( * ) Notice: Subject to any disclaimer, the term of this patent is extended or adjusted under 35 U.S.C. 154(b) by 54 days.

(21) Appl. No.: 18/529,682

(22) Filed: Dec. 5, 2023

(65) Prior Publication Data

US 2024/0099885 A1    Mar. 28, 2024

Related U.S. Application Data

(63) Continuation of application No. 17/015,182, filed on Sep. 9, 2020, now Pat. No. 11,883,325.

(60) Provisional application No. 62/900,756, filed on Sep. 16, 2019.

(51) Int. Cl.
*A61F 9/007* (2006.01)
*A61B 17/00* (2006.01)

(52) U.S. Cl.
CPC .. *A61F 9/00745* (2013.01); *A61B 2017/0042* (2013.01); *A61B 2017/00544* (2013.01); *A61B 2017/00694* (2013.01)

(58) Field of Classification Search
CPC ......... A61F 9/00763; A61F 2250/0075; A61B 17/32002; A61B 2017/320028; A61B 2017/0042; A61B 2017/00544; A61B 2017/00535; A61B 2017/00694
See application file for complete search history.

(56) References Cited

U.S. PATENT DOCUMENTS

| | | | | |
|---|---|---|---|---|
| 5,630,826 | A | * 5/1997 | Sastri | A61B 17/32002 |
| | | | | 606/180 |
| 2008/0281277 | A1 | 11/2008 | Thyzel | |
| 2012/0157906 | A1 | 6/2012 | Underwood et al. | |
| 2012/0157934 | A1* | 6/2012 | Liao | A61F 9/00745 |
| | | | | 604/264 |
| 2012/0316490 | A1* | 12/2012 | Perkins | A61F 9/00745 |
| | | | | 604/22 |
| 2016/0120699 | A1 | 5/2016 | Farley | |
| 2018/0243134 | A1* | 8/2018 | Dean | A61F 9/00763 |
| 2018/0360660 | A1* | 12/2018 | Lopez | A61F 9/00763 |

(Continued)

FOREIGN PATENT DOCUMENTS

| | | |
|---|---|---|
| JP | 2009/525782 A | 7/2009 |
| JP | 2017509419 A | 4/2017 |
| WO | 2018/234906 A1 | 12/2018 |

*Primary Examiner* — Diane D Yabut
(74) *Attorney, Agent, or Firm* — Patterson + Sheridan, LLP

(57) ABSTRACT

A vitrectomy probe with combined vibration dampening and attenuating. The probe may include a variety of features to lessen the vibrations felt by a surgeon during a vitrectomy procedure. These may include minimizing the degree of flow restriction through a housing that facilitates cutter reciprocation by way of air pressure. Further, utilizing softer stops at a diaphragm that drives the cutter reciprocation may be of benefit as is strategically lessening compressive forces by seals at an extension tube coupled to the diaphragm where possible. The use of a softer gripping component that is actually held by the surgeon may be of benefit in terms of vibration attenuation.

20 Claims, 6 Drawing Sheets

(56)     References Cited

U.S. PATENT DOCUMENTS

2019/0290314  A1     9/2019   Gemer et al.
2020/0261266  A1     8/2020   Bley et al.

* cited by examiner

REDUCED VIBRATION VITRECTOMY PROBE

PRIORITY CLAIM

This application is a continuation of U.S. Non-Provisional patent application Ser. No. 17/015,182, filed on Sep. 9, 2020, which claims priority to and benefit of U.S. Provisional Patent Application No. 62/900,756, filed Sep. 16, 2019, which is hereby incorporated by reference in its entirety as though fully and completely set forth herein.

BACKGROUND

Over the years, many dramatic advancements in the field of retinal eye surgery have taken place. However, regardless of the particular retinal procedure, it is common that a vitrectomy will be included in at least part of the procedure. Vitrectomy is the removal of some or all of the vitreous humor from a patient's eye. In some cases, where the surgery was limited to removal of clouded vitreous humor, the vitrectomy may constitute the majority of the procedure. However, a vitrectomy may also accompany cataract surgery, surgery to repair a retina, to address a macular pucker or a host of other issues.

The vitreous humor itself is a clear gel that may be removed by an elongated probe when inserted through a pre-placed cannula at the eye. More specifically, the probe includes a central channel for removal of the vitreous humor. Further, the cannula provides a structurally supportive conduit strategically located at an offset location at the front of the eye, such as the pars plana. In this way, the probe may be guidingly inserted into the eye in a manner that avoids damage to the patient's lens or cornea.

Unfortunately, removal of the vitreous humor requires greater care than simply applying a vacuum through the channel of the probe. This is because the vitreous humor includes a fibrous matrix of collagen fibrils. Therefore, merely applying a vacuum to the gel would place the surrounding eye structure in jeopardy. That is, the fibrous nature of the gel is such that a vacuum pull on the gel into the probe might translate into a pull on the retina, optic nerve or other delicate eye structures.

In order to address this issue, vitrectomy probes are configured to cut vitreous humor as it is drawn into the channel of the probe. In this way, a continuous fibrous pull on the gel-like substance does not translate into a pull on delicate eye structures. Instead, the vitreous humor is pulled into the channel of the probe in very small, chopped segments. This chipping or cutting of the vitreous humor occurs by the reciprocation of a cutter within the channel of the probe. More specifically, the cutter reciprocates back and forth at a port for intake of the vitreous humor in a manner that cuts the substance as it is being drawn into the channel. Perhaps 5,000 to 10,000 cycle cuts per minute may take place in this manner in order to safeguard the eye from pulling by the vitreous humor as it is being removed. Indeed, the faster the cutter reciprocates, the greater the degree of vitreous humor cutting occurs with less traction. Thus, a greater the degree of protection is provided to the patient's delicate eye features as described.

Along these lines, cutter reciprocation has become faster and faster over the years. Thus, the concern over "pull" on the vitreous humor during a vitrectomy procedure has largely been eliminated. However, reciprocating a cutter in this manner means that during the vitrectomy, vibrations are naturally translated through the vitrectomy probe. Therefore, the surgeon that is manually carrying out the procedure faces the prospect of a vibration related distraction while manipulating the probe in tight delicate spaces.

SUMMARY

A vitrectomy probe is disclosed. In one embodiment, the probe includes a component housing. A diaphragm within a chamber of the housing is configured for reciprocating at a rate of at least about 2,500 cuts per minute (cpm) during a vitrectomy procedure wherein the reciprocating includes repeated striking by the diaphragm at walls defining the chamber. First and second channels of air are used to reciprocate the diaphragm at first and second sides thereof wherein the channels have a volume of at least about $0.00275$ in$^3$ to minimize flow restriction to facilitate air pressure being less than about 50 pounds per square inch (PSI) for dampening of the striking.

In another embodiment, the probe includes a component housing with an extension tube positioned in a channel thereof for reciprocating in response to alternating supplies of air pressure during a vitrectomy procedure. This facilitates the cutting of vitreous humor. A first seal ring about the extension tubing exerts a first compression load against the tube to seal off the channel from air pressure directing the reciprocating. At the same time, a second seal ring about the extension tube exerts a second compression load against the tube to seal off the channel from a vacuum. The second compression load is substantially less than the first compression load to decrease the amount of air pressure utilized for the reciprocating.

BRIEF DESCRIPTION OF THE DRAWINGS

FIG. 2 1s a perspective view of the reduced vibration vitrectomy probe m assembled form.

DETAILED DESCRIPTION

In the following description, numerous details are set forth to provide an understanding of the present disclosure. However, it will be understood by those skilled in the art that the embodiments described may be practiced without these particular details. Further, numerous variations or modifications may be employed which remain contemplated by the embodiments as specifically described.

Embodiments are described with reference to certain types of vitrectomy probe surgical procedures. In particular, a procedure in which vitreous humor is removed to address vitreous hemorrhage is illustrated. However, tools and techniques detailed herein may be employed in a variety of other manners. For example, embodiments of a vitrectomy probe as detailed herein may be utilized to address retinal detachments, macular pucker, macular holes, vitreous floaters, diabetic retinopathy or a variety of other eye conditions. Regardless, so long as the vitrectomy probe incorporates vibration reduction features as detailed herein, appreciable benefit may be realized.

Figure 1:
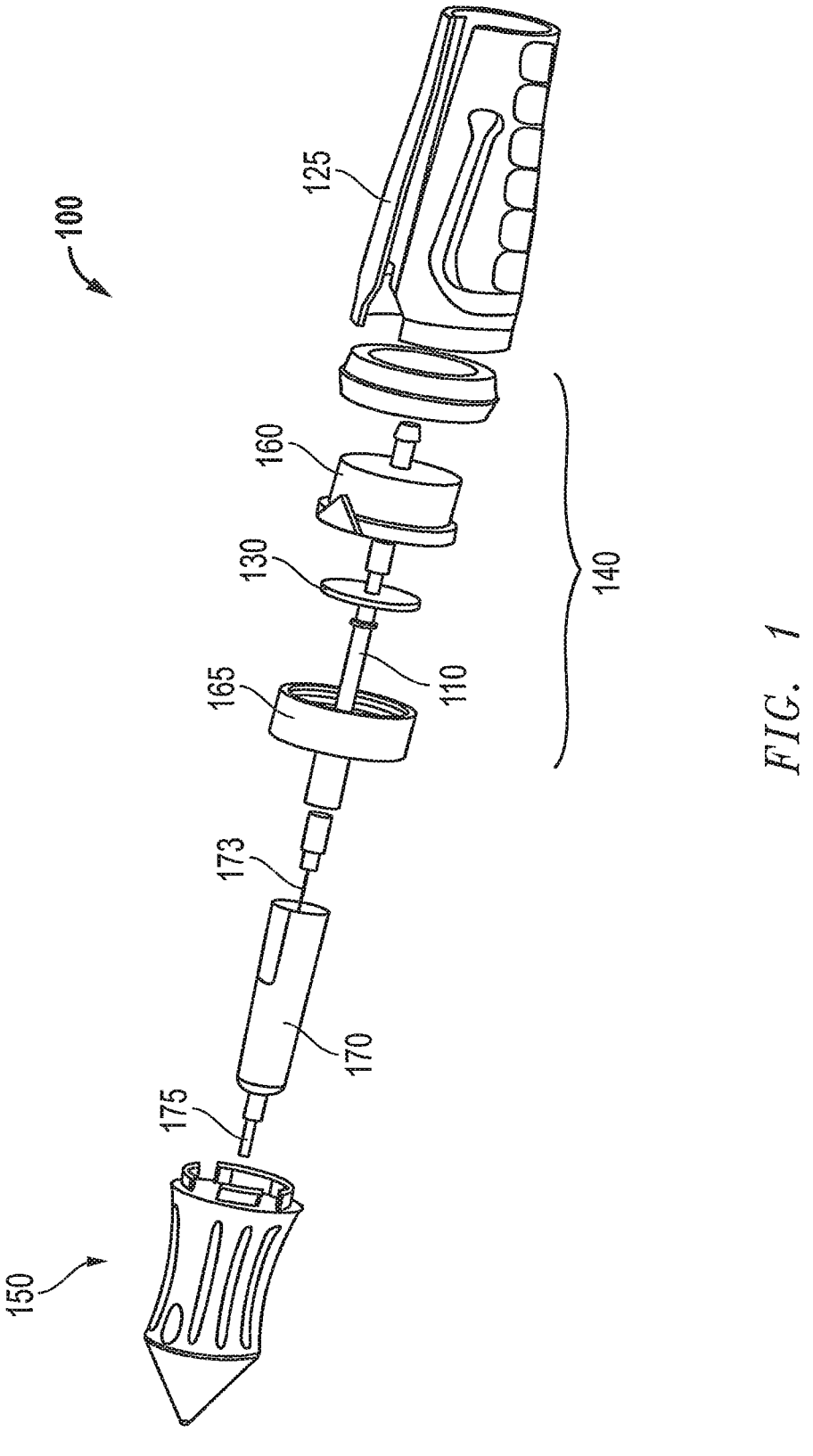
FIG. 1 is an exploded perspective view of an embodiment of a reduced vibration vitrectomy probe.

Referring now to FIG. 1, an exploded perspective view of an embodiment of a reduced vibration vitrectomy probe 100 is shown. A variety of features are incorporated into the probe 100 for sake of vibration reduction as noted. For example, a gripping component 150 is provided with enhanced ergonomics. Specifically, given that this component 150 is in direct contact with the surgeon's hand during a vitrectomy procedure, providing a soft touch feature may help to attenuate and minimize the amount of vibration that reaches the surgeon. For example, in the embodiment shown, the gripping component may be constructed of a conventional elastomer having a hardness of less than about 60 Shore A This is in sharp contrast to conventional gripping components which are generally a hard polycarbonate over mold.

In another departure from conventional gripping components, the illustrated component 150 may be of a reduced diameter that is less than about 0.5 inches. The smaller diameter in combination with the soft touch gripping component 150 may allow for a finer finger tip control with more room for manual complex maneuvering.

In addition to the gripping component 150, a variety of other vibration reduction features are incorporated into the probe 100. For example, sticking with the notion of softer material choices, the illustrated diaphragm 130 reciprocates between housing components 160, 165 of the probe housing 140 in ultimately driving the movement of a cutter 173 within a needle 175. During this reciprocation of the diaphragm 130, it repeatedly strikes each of the housing components 160, 165. More specifically, discrete stops 450 of the diaphragm 130 may repeatedly hit the housing components 160, 165 which result in the noted vibrations (see FIG. 4). Nevertheless, in one embodiment, the stops 450 are made of a soft silicone rubber or other suitable material having a hardness of less than about 60 Shore A Thus, vibration may not only be attenuated but generated to a smaller degree in the first place.

Continuing with reference to FIG. 1, an ergonomic shell 125 is shown at one end of the probe 100 that may rest at a surgeon's hand during a vitrectomy procedure. Near the other end of the probe 100, a coupling 170 is shown secured over the cutter 173 at the front of the forward housing component 165. However, rearward of the forward housing component 165 is the extension tube 110 which accommodates the cutter 173 during the vitrectomy procedure. As detailed further below, the extension tube 110 is uniquely configured to reduce friction during reciprocation. As a result, the amount of force required to reciprocate the diaphragm 130 and tube 110 is reduced in a manner that further dampens the impact of the repeated striking of the diaphragm 130 at each housing component 160, 165.

Figure 2:
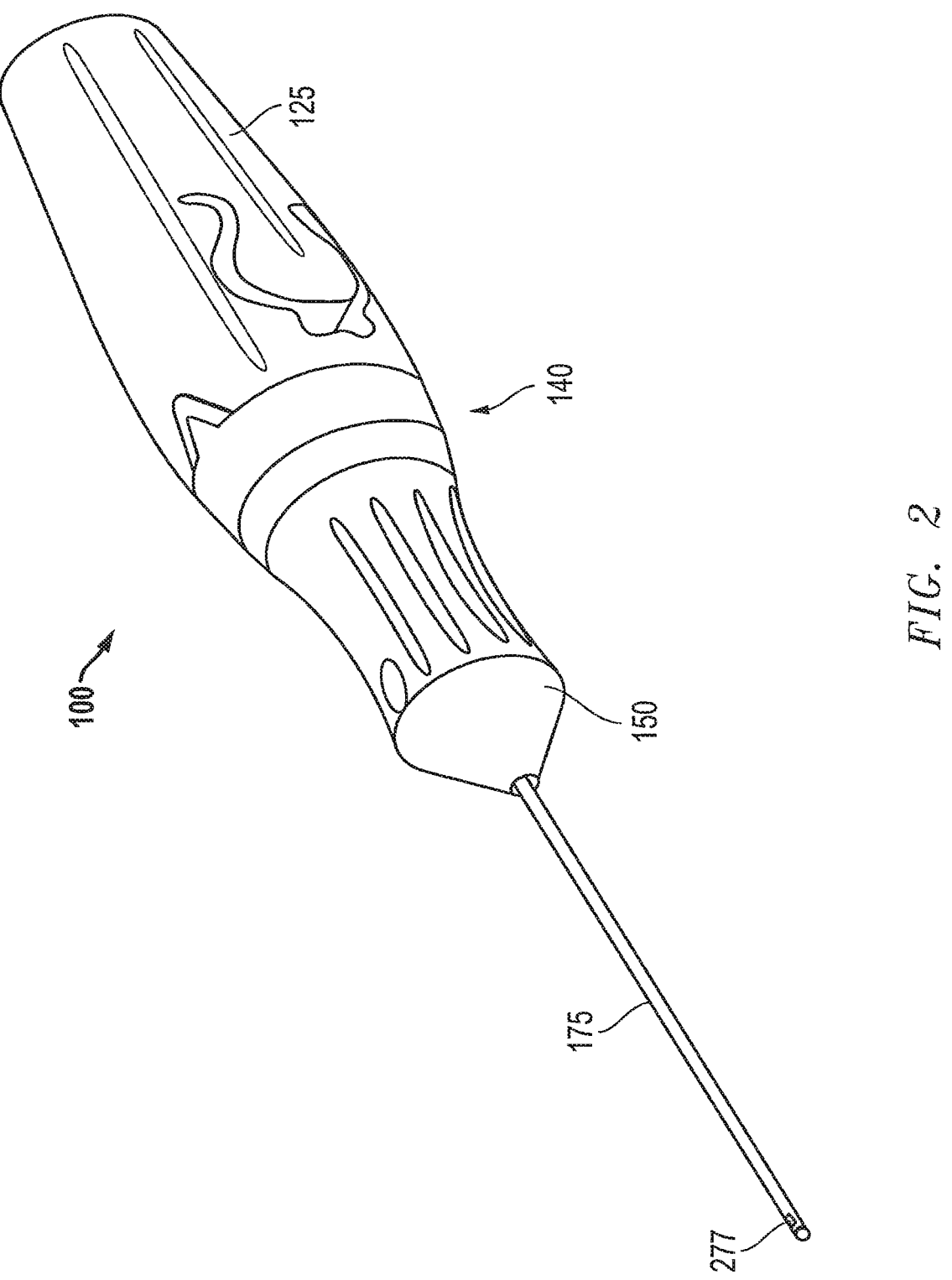

Referring now to FIG. 2, a perspective view of the reduced vibration vitrectomy probe 100 is shown in assembled form. In this view, the port 277 through which vitreous humor is drawn into the needle 175 of the probe 100 is shown in front of the soft touch gripping component 150. This component 150 is secured to the housing 140 with the shell 125 fitted onto the housing 140 as well. Thus, from a surgeon's perspective, a unitary handheld surgical tool is provided with reduced vibrational distraction.

Figure 3A:
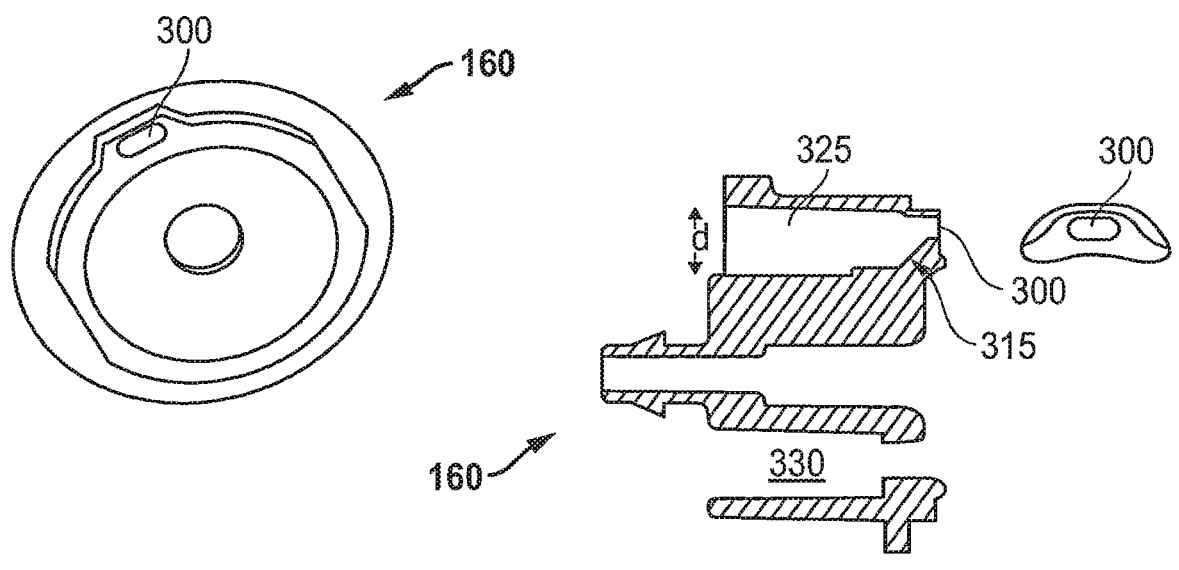
FIG. 3A is a side cross-sectional view of an embodiment of an internal rear housing component of the vitrectomy probe of FIG. 2 with stepped channeling.

In terms of reducing vibrational distraction for the surgeon, another feature is provided that is not readily apparent from outside views of the probe 100. Specifically, FIG. 3A is a side cross-sectional view of an embodiment of the internal rear housing component 160 of the vitrectomy probe of FIG. 2 with stepped channeling 315. That is, reciprocating the diaphragm 130 of FIG. 1 is achieved by way of air pressure directed at either side of the diaphragm 130 in an alternating manner. More specifically, with added reference to FIG. 1, air through a lower chamber 330 might be directed at the back side of the diaphragm 130 to push the extension tube 110 forward and advance the cutter 173. Alternatively, air through an upper chamber 325 might be ultimately routed to the front side of the diaphragm 130 to ultimately force the cutter 173 to retract away from the end of the needle 175.

Figure 3B:
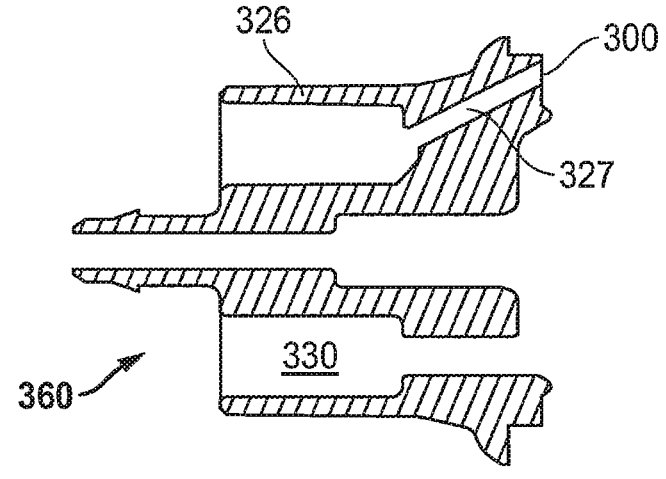
FIG. 3B is a side cross-sectional view of a prior art internal rear housing component for a vitrectomy probe employing conventional uniform channeling.

Due to the added routing involved in the upper chamber 325, air reaching the opposite front side of the diaphragm 130, conventional architecture was to provide a uniform channel 327 through the rear housing 160 (see FIG. 3B). However, for the embodiment of FIG. 3A, this type of channeling has been replaced with stepped channeling 315 so as to substantially avoid presenting a flow restriction. As a result, the diaphragm 130 of FIG. 1 may be reciprocated in a rearward direction with less air pressure without compromising the overall rate of reciprocation. For example, in one embodiment, stepped channeling 315 as depicted allows for less than 50 PSI to be applied while still achieving a reciprocation rate of 2,500 cpm. In one embodiment, less than 15 PSI may be sufficient to achieve a rate of greater than 2,500 cpm. With this substantial decrease in air pressure driving the reciprocation, a corresponding decrease in striking of the diaphragm 130 at the housing walls also results. Thus, an added degree of minimizing distracting vibrations during a vitrectomy is seen.

Figure 4:
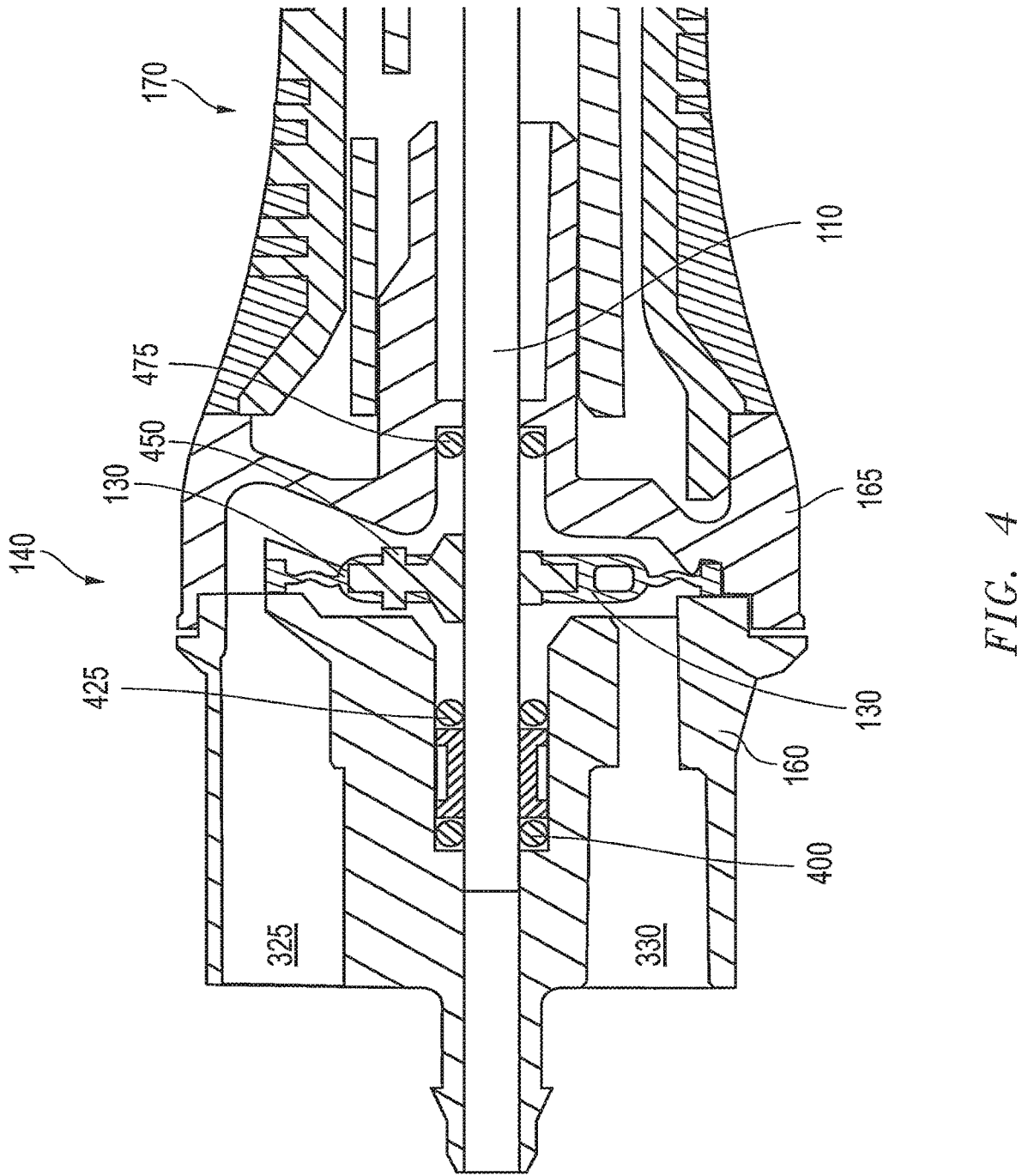
FIG. 4 is a side cross-sectional view of the internal rear housing of FIGS. 3A and 3B secured to an internal forward housing and accommodating an extension tube in a reduced frictional manner.

As illustrated here and in FIG. 4, the stepped channeling 315 is part of the diaphragm front side flow path that includes the upper chamber 325 with a volume of at least about 0.00275 in³. However, in contrast to the prior art of FIG. 3B, the primary distinction is the substantial elimination of a uniform channel 327 in reaching the outlet 300. That is while the inlet at (d) and the outlet 300 may be of roughly the same sizing in the prior art of FIG. 3B and in the embodiment of FIG. 3A, the latter is free of the flow restricting uniform channel 327 in reaching the outlet 300. Instead, a stepped channel 315 is provided.

Figure 5:
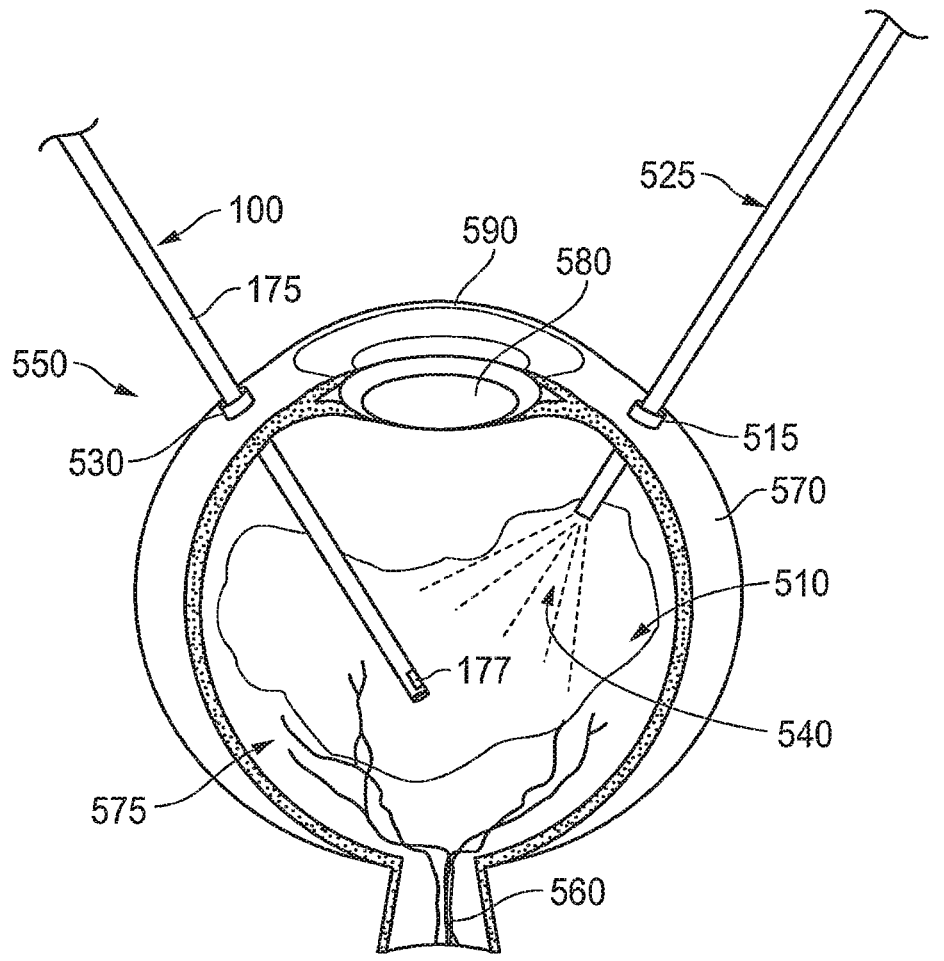
FIG. 5 is an overview of an embodiment of a vitrectomy surgery performed with the vitrectomy probe of FIG. 2.

Referring specifically now to FIG. 4, a side cross-sectional view of the internal rear housing 160 of FIGS. 3A and 3B is depicted secured to the internal forward housing 165 and accommodating the extension tube 110 in a reduced frictional manner. That is, as described above, the diaphragm 130 is alternatingly reciprocated in response to air pressure through one chamber 325 or another 330. This reciprocation moves the extension tube 110 back and forth ultimately providing the cutting function for the vitreous humor (e.g. see the surgical depiction of FIG. 5). Regardless, the use of air pressure in this manner means that seals 400, 425, 475 may be disposed about the tube 110 at various locations within the housing 140. For example, this may prevent the potentially catastrophic event of accidentally directing high pressure air into a patient's eye 550 during a surgery as illustrated in FIG. 5.

The use of seals 400, 425, 475 in this manner means that frictional resistance to reciprocation of the tube 110 may be introduced. Ultimately, this could translate into the need to utilize higher pressures to drive reciprocation that in turn would mean higher striking forces by the stops 450 and thus, a higher degree of vibrations produced. However, for the embodiment depicted in FIG. 4, this frictional resistance is strategically reduced. More specifically, the embodiment of FIG. 4 acknowledges that it is only the forward most seal 475 that actually plays a role in protecting the patient's eye 550 during surgery as depicted in FIG. 5. This is because only the return stroke as directed through the upper channel 325 has the potential to reach the patient's eye 550 if not sealed by the forward seal 475 (see FIG. 5). The other air passages, are sealed by the front of the diaphragm 130 itself (e.g. see channel 330) or involve a vacuum through the center of the tube 110 that removes the vitreous humor. If either of these seals 400, 425 fails to perform, the patient's eye 550 is not placed in peril (see FIG. 5).

With this in mind, embodiments of the extension tube 110, seals 400,425,475 and surrounding architecture may be configured to reduce overall friction at the seal-tube interface without sacrifice to patient safety. For example, in one embodiment, the outer diameter of the tube may be reduced to below about 0.05 inches and electro-polished without altering dimensions of the inner diameter of the rearward seals 400, 425. Similarly, utilizing seals 400, 425, 475 with a hardness of below about 70 shore A may minimize friction. The more critical forward seal 475 may be reduced in inner diameter for sake of patient safety. However, the overall frictional resistance would still be substantially reduced in a manner that would reduce air pressure and striking force of the vibration producing stops 450 as detailed above.

In the above described embodiment, the change in tube 110 outer diameter may not be accompanied by any substantial change in inner diameter. For example, where a conventional inner diameter of the extension tube might be about 0.035 inches, the tube 110 might retain this same inner diameter. The result is not just to retain the functional capability of the tube 110 in vitreous humor uptake but also to provide a tube 110 that is thinner (e.g. about 0.0010 inches in diameter). As a result, a lighter tube is provided, further reducing the necessary air pressure reciprocation forces and resulting vibrational strikes by the stops 450 described herein.

In another embodiment, reducing the force of the noted strikes and resulting vibrations may be achieved by reducing the amount of distance traveled by the stops 450. For example, as illustrated, with the diaphragm 130 centered, the distance between the stops 450 and adjacent housing structure at either side thereof may be about 0.015 inches with a total travel distance of 0.030 inches. However, with no flow path interference for the stop 450 at the top rear of the diaphragm 130, this distance may be reduced, for example to 0.005 inches, such that the total travel distance is limited to 0.020 inches. Thus, the force of strikes and resulting vibrations from this stop location may be reduced. Similarly, the inverse may be true of stops at the lower part of the diaphragm 130, with a backside stop having a greater travel distance (e.g. 0.015 inches) due to the presence of a flow path but the front side stop having a lesser travel distance (e.g. 0.005 inches). Stated another way, stop travel distance may be reduced by having a shorter distance between each non-flow path stop and adjacent housing structure than between each flow path stop and adjacent housing structure.

Additional measures for reducing friction at the tube 110 may include placing silicone lubricant at the inner diameter of the seals 400, 425, 475. This may include the placement of such a lubricant at a seal interfacing the cutter 173 within or near the entrance to the needle 175 as illustrated in FIG.

1. In such embodiments, the seals 400, 425, 475 may also be of a parylene coated polymer or a polytetrafluoroethylene coating.

Referring now to FIG. 5, an overview of an embodiment of a vitrectomy surgery performed with the vitrectomy probe 100 of FIG. 2 is illustrated. In this view, the vitrectomy probe 100 of FIG. 2, with the cutter 173 of FIG. 1, is utilized. During this surgical procedure, the needle 175 is inserted through a preplaced cannula 530 and directed toward a region 510 where vitreous humor is to be removed. Specifically, as described above, a suction is applied and the port 177 is used for the uptake of the vitreous humor or other substances. For example, in the procedure illustrated, a hemorrhage may be taking place in the region 510 such that blood is drawn into the port 177 along with the vitreous humor.

With added reference to FIGS. 1 and 4, as also described above, a cutter 173 is reciprocating within the needle 175 during this delicate procedure. This means that a diaphragm 130 within the housing 140 is repeatedly reciprocating the cutter 173, likely in excess of 10,000 times per minute. In spite of this reciprocation and tremendous number of strikes by stops 450 of the diaphragm 130 at housing structure, vibrations are kept to a minimum by the various features of the probe 100 as detailed herein. From the surgeon's perspective, and for the benefit of the patient, potentially distracting noise has been mitigated during the surgery.

Continuing with reference to FIG. 5, the illustrated surgery includes the probe 101 and a light instrument 525 reaching into the eye 550 through cannulas 515, 530 positioned in an offset manner at the sclera 570. In this way, the more delicate cornea 590 and lens 580 may be avoided. By the same token, the optic nerve 560 and retina 575 are also quite delicate. Therefore, given that the needle 175 is capable of reaching these delicate features, the light instrument 525 may be used to illuminate both the back of the eye 550 and the end of the needle 175 for the surgeon.

Figure 6:
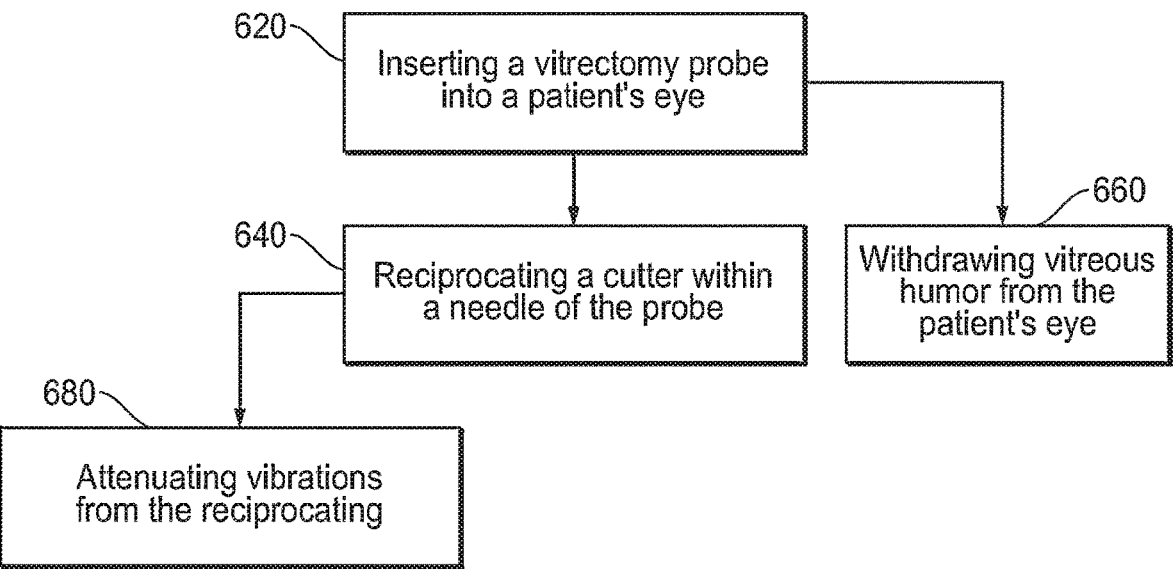
FIG. 6 is a flow-chart summarizing an embodiment of employing a reduced vibration vitrectomy probe in a surgical procedure.

Referring now to FIG. 6, a flow-chart summarizing an embodiment of employing a reduced vibration vitrectomy probe in a surgical procedure is shown. With a probe inserted as illustrated in FIG. 5 and noted at 620, vitreous humor may be withdrawn from the patient's eye as indicated at 660. This is achieved through reciprocation of a cutter within a needle of the probe (see 640). As indicated at 680, this reciprocation is accompanied by an attenuating of vibration due to the reciprocation. Whether by way of a soft grip, stepped channel air pressure, diminished friction at an extension tube, a silicone rubber stop with shortened travel distance or a variety of additional measures, appreciable benefit may be realized.

Embodiments described hereinabove include a vitrectomy probe with a variety of features and enhancements tailored to attenuate potentially distracting vibrations from a surgeon's perspective. In each case, the reduction in vibration is achieved without sacrificing reciprocation rate for a cutter of the vitrectomy probe. Thus, the vibration reduction is attained in a manner that does not compromise the effectiveness of the probe for the surgical procedure at hand.

The preceding description has been presented with reference to various embodiments. However, other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

What is claimed is:

1. A vitrectomy probe comprising:
a forward housing component;
a rearward housing component;
a diaphragm located in a space between and defined by the forward housing component and the rearward housing component for reciprocating therebetween in response to air flows alternatingly directed at opposite sides of the diaphragm;
a plurality of discrete stops for striking the forward housing component and the rearward housing component during the reciprocating, the striking resulting in vibrations, at least a subset of the plurality of discrete stops comprising a material that is less than about 60 Shore A in hardness to dampen the vibrations;
a cutter coupling to the diaphragm and located within a needle of the vitrectomy probe to cut vitreous humor during a vitrectomy procedure performed by a surgeon;
a gripping component with the needle emerging therefrom, the gripping component coupled to the forward housing component and for manual holding by the surgeon during the vitrectomy procedure, the gripping component comprising an elastomer that is less than about 60 Shore A in hardness to attenuate the vibrations; and
a shell coupled to the rearward housing component,
wherein the forward housing component and the rearward housing component are disposed between the shell and the gripping component and form at least a portion of an exterior surface of the vitrectomy probe.

2. The vitrectomy probe of claim 1, wherein the gripping component is less than about 0.5 inches in outer diameter.

3. The vitrectomy probe of claim 1, wherein the plurality of discrete stops are comprised of silicone rubber.

4. The vitrectomy probe of claim 1, further comprising an extension tube to facilitate the coupling of the cutter to the diaphragm, the extension tube configured to reciprocate with the diaphragm and the cutter during the vitrectomy in response to the air flows.

5. The vitrectomy probe of claim 4, further comprising static seals mounted in the forward housing component and the rearward housing component about the extension tube for sealing off the air flows.

6. The vitrectomy probe of claim 5, wherein the static seals that do not seal off an air flow directing the diaphragm away from the forward housing component present less compressive force on the extension tube than any seal that does seal off the air flow directing the diaphragm away from the forward housing component.

7. The vitrectomy probe of claim 5, wherein the static seals are coated with one of a parylene polymer and polytetrafluoroethylene.

8. The vitrectomy probe of claim 5, wherein the extension tube is electro-polished.

9. The vitrectomy probe of claim 5, further comprising silicone lubricant at interfaces between the extension tube and the static seals.

10. The vitrectomy probe of claim 1, wherein the rearward housing component accommodates a first air flow therethrough for directing a diaphragm to travel toward a needle of a vitrectomy probe.

11. The vitrectomy probe of claim 1, wherein the forward housing component accommodates a second air flow therethrough for directing the diaphragm to travel away from the needle of the probe, the rearward housing having a stepped channel to accommodate the second air flow therethrough in advance of reaching the forward housing.

12. The vitrectomy probe of claim 11, wherein the stepped channel is at a chamber of the rearward housing with a volume of at least about 0.00275 in³.

13. The vitrectomy probe of claim 1, wherein an outlet at a most distal portion of the rearward housing has a longitudinal axis that is parallel to an axis of the most proximal portion of an airflow path through the rearward housing.

14. The vitrectomy probe of claim 1, wherein the rearward housing is uniform channel free to minimize flow restriction of the air flows therethrough.

15. A method of performing a vitrectomy, the method comprising:
inserting a needle of a vitrectomy probe into an eye of a patient with a hand of a surgeon, wherein the vitrectomy probe comprises:
a forward housing component;
a rearward housing component;
a gripping component with the needle emerging therefrom, the gripping component coupled to the forward housing component; and
a shell coupled to the rearward housing component,
wherein the forward housing component and the rearward housing component are disposed between the shell and the gripping component and form at least a portion of an exterior surface of the vitrectomy probe; and
withdrawing vitreous humor from the eye through a port of the needle;
reciprocating a cutter within the needle to cut the vitreous humor as it enters the needle;
dampening a degree of produced vibrations due to the reciprocating of the cutter; and
attenuating an amount of produced vibrations reaching the surgeon's hand.

16. The method of claim 15, wherein the dampening of the produced vibrations comprises utilizing a stepped channel to minimize flow restriction in a housing accommodating reciprocating components for the cutter.

17. The method of claim 16, wherein the dampening of the produced vibrations comprises utilizing discrete silicone stops at a diaphragm driving the reciprocating, the discrete silicone stops striking a structure of the housing during the reciprocating.

18. The method of claim 17, wherein the dampening of the degree of produced vibrations comprises using seals at an extension tube coupling the diaphragm to the cutter wherein compressive force on the extension tube is less for any seal not sealing off an air flow directing a return stroke of the diaphragm away from the eye of the patient than for any seal sealing off the air flow directing the return stroke of the diaphragm away from the eye of the patient.

19. The method of claim 15, wherein the attenuating of the amount of produced vibrations is achieved through a gripping component of the vitrectomy probe in the hand of the surgeon during the vitrectomy, the gripping component comprised of an elastomer that is less than about 60 Shore A in hardness.

20. The method of claim 15,
wherein the rearward housing component accommodates a first air flow therethrough for directing a diaphragm to travel toward a needle of a vitrectomy probe; and wherein the forward housing component accommodates a second air flow therethrough for directing the diaphragm to travel away from the needle of the probe, the rearward housing having a stepped channel to accommodate the second air flow therethrough in advance of reaching the forward housing;

wherein an outlet at a most distal portion of the rearward housing has a longitudinal axis that is parallel to an axis of the most proximal portion of an airflow path through the rearward housing.

\* \* \* \* \*